United States Patent [19]
Wung et al.

[11] Patent Number: 5,623,931
[45] Date of Patent: Apr. 29, 1997

[54] NEEDLE GUIDE FOR USE WITH ULTRASOUND IMAGING SYSTEMS

[75] Inventors: Peter C. Wung, Redmond; Marc W. Bommarito, Maple Valley; John G. Tomkinson, Seattle; Swend L. Miller, Kent, all of Wash.

[73] Assignee: Siemens Medical Systems, Inc., Iselin, N.J.

[21] Appl. No.: 321,646

[22] Filed: Oct. 11, 1994

[51] Int. Cl.$^6$ .................................................. A61B 8/00
[52] U.S. Cl. .................................................. 128/662.05
[58] Field of Search ............... 128/662.05, 662.06; 606/130, 151, 181–183; 248/231.7, 231.8, 316.1, 316.3, 316.7

[56] References Cited

U.S. PATENT DOCUMENTS

| | | | |
|---|---|---|---|
| 4,230,118 | 10/1980 | Holman et al. | 606/182 |
| 4,397,438 | 8/1983 | Chapman | 248/231.8 |
| 4,628,929 | 12/1986 | Intengen et al. | 606/182 |
| 4,899,756 | 2/1990 | Sonek | 128/662.05 |
| 5,052,396 | 10/1991 | Wedel et al. | 128/662.05 |
| 5,076,279 | 12/1991 | Arenson et al. | 128/662.05 |
| 5,160,105 | 11/1992 | Miller | 248/231.8 |

*Primary Examiner*—Max Hindenburg

[57] ABSTRACT

An embodiment of the present invention is a disposable/reusable needle guide which can be: (a) utilized with many ultrasound probes; (b) attached and detached from such ultrasound probes easily and rapidly; and (c) utilized with biopsy needles. In particular, an embodiment of the present invention is a needle guide for use with an ultrasound probe which includes: (a) a clip for detachably affixing the needle guide to the ultrasound probe; (b) a clip lock for detachably locking the clip to securely affix the needle guide to the ultrasound probe; (c) a needle support, affixed to the clip, for supporting and positioning a needle; and (d) a needle cap, detachably affixed to the needle support, for supporting and positioning the needle; wherein the needle support and the needle cap include a snap locking for detachably affixing the needle support and the needle cap to each other.

11 Claims, 3 Drawing Sheets

NEEDLE GUIDE FOR USE WITH ULTRASOUND IMAGING SYSTEMS

TECHNICAL FIELD OF THE INVENTION

The present invention relates to a disposable/reusable needle guide for use in conjunction with an ultrasound imaging system.

BACKGROUND OF THE INVENTION

It is well known in the industry that ultrasound imaging systems are useful for performing a surgical procedure such as a biopsy. In such a use, the ultrasound imaging system is used to locate a region of interest and a biopsy needle is inserted into that region. Advantageously, the biopsy needle is visible during the surgical procedure.

In the past, in such a use, a biopsy guide was utilized to aid in positioning and holding the biopsy needle. The biopsy guide was affixed to an ultrasound probe by a clamp which surrounded the probe and which was designed to fit a specific probe. This is disadvantageous because of the need to utilize different guides for different probes and because of the time and difficulty entailed in attaching and detaching the biopsy guide.

In light of the above, there is a need in the art for a disposable/reusable needle guide (also for use as a biopsy guide) which can be: (a) utilized with different ultrasound probes; (b) attached and detached from such ultrasound probes easily and rapidly; and (c) utilized with biopsy needles.

SUMMARY OF THE INVENTION

Advantageously, an embodiment of the present invention is a disposable/reusable needle guide that can be: (a) utilized with many ultrasound probes; (b) attached and detached from such ultrasound probes easily and rapidly; and (c) utilized with biopsy needles. In particular, an embodiment of the present invention is a needle guide for use with an ultrasound probe which comprises: (a) clip means for detachably affixing the needle guide to the ultrasound probe; (b) clip lock means for detachably locking the clip means to securely affix the needle guide to the ultrasound probe; (c) needle support means, affixed to the clip means, for supporting and positioning a needle; and (d) needle cap means, detachably affixed to the needle support means, for supporting and positioning the needle; wherein the needle support means and the needle cap means are comprised of snap locking means for detachably affixing needle support means and needle cap means to each other.

DETAILED DESCRIPTION

Figure 1:
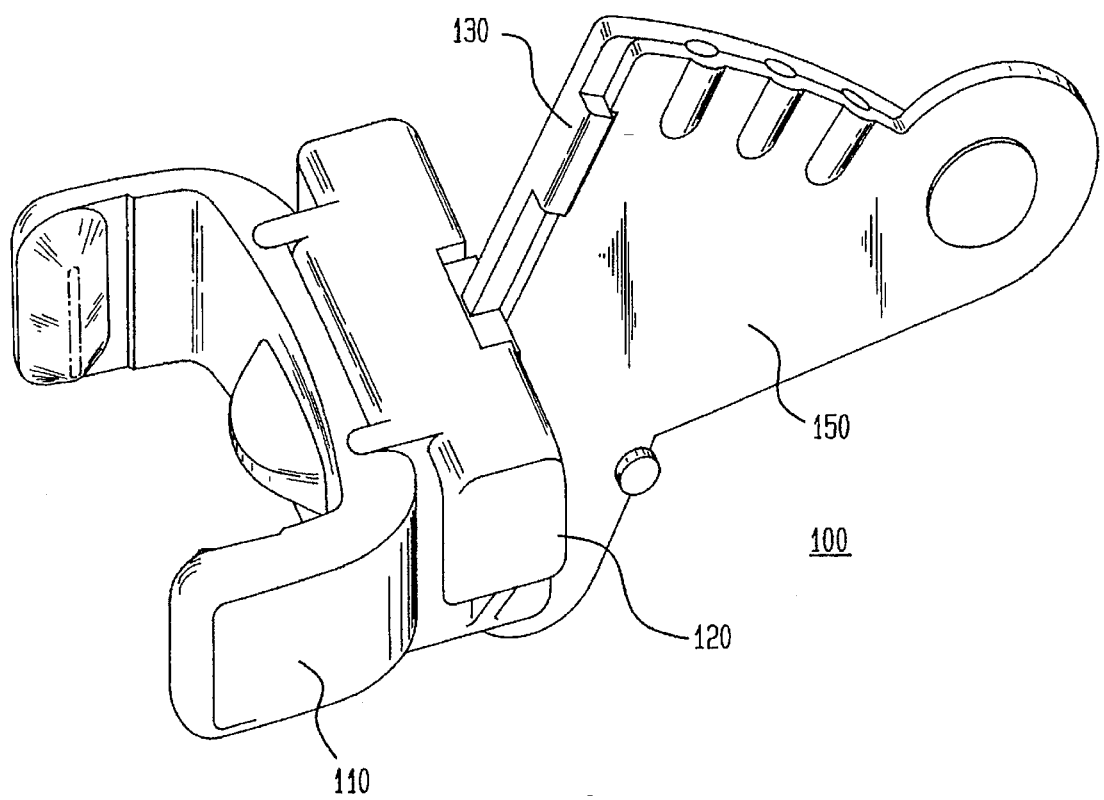
FIG. 1 shows a perspective view of a needle guide which is fabricated in accordance with the present invention and which is comprised of: (a) a probe clip; (b) a probe clip lock; (c) a needle support; and (d) a needle cap.

FIG. 1 shows a perspective view of an embodiment of the present invention, i.e., inventive needle guide 100. As shown in FIG. 1, needle guide 100 is comprised of: (a) probe clip 110; (b) probe clip lock 120; (c) needle support 130; and (d) needle cap 150. In a preferred embodiment of the present invention, probe clip 110, probe clip lock 120, needle support 130, and needle cap 150 are formed by injection molding plastic in a manner which is well known in the art. After the parts are produced by injection molding, probe clip lock 120 is slidably joined to needle support 130 in a manner that will be described in detail below and needle support 130 is ultrasonically welded to probe clip 110 so that probe clip lock 120 is constrained to slide in a confined location. Finally, needle cap 150 is detachably affixed to needle support 130 in a manner that will be described in detail below.

Figure 6:
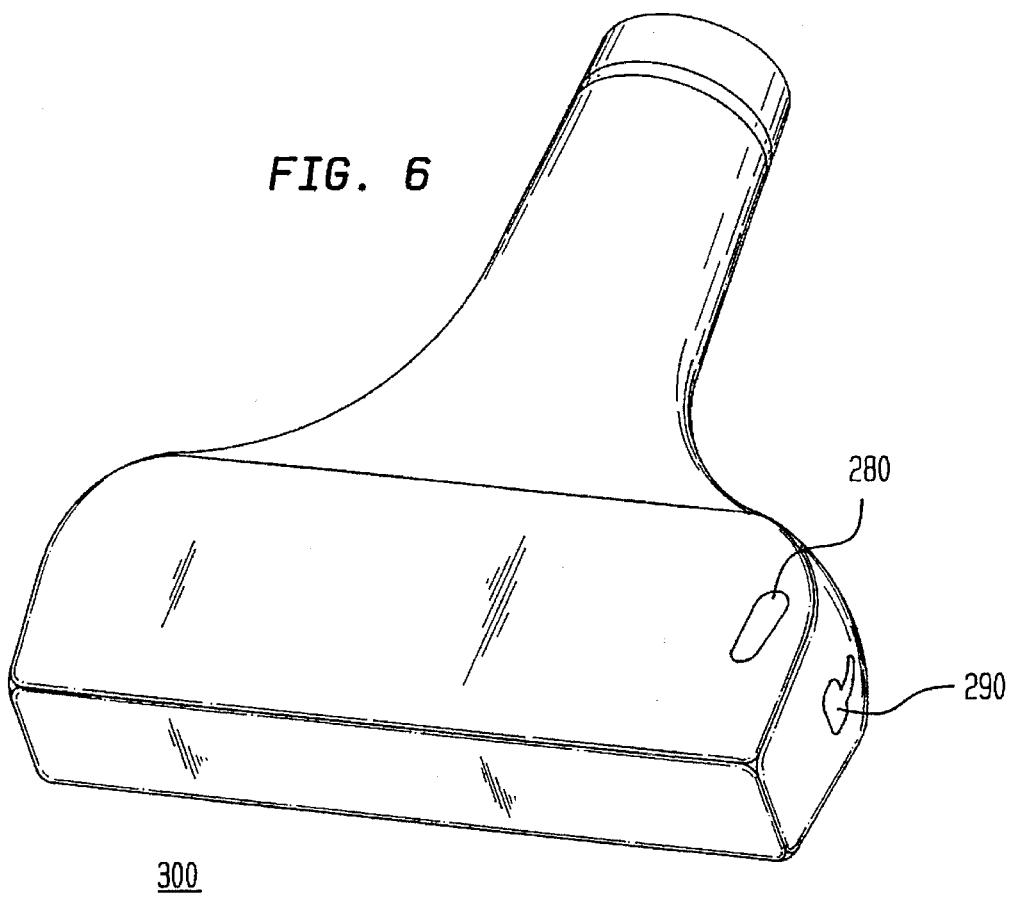
FIG. 6 shows, in pictorial form, a perspective view of an ultrasound probe which is used in conjunction with the inventive needle guide.

FIG. 6 shows, in pictorial form, a perspective view of ultrasound probe 300 which is used in conjunction with inventive needle guide 100. The manner in which needle guide 100 is affixed to ultrasound probe 300 will be described in detail below.

Figure 2:
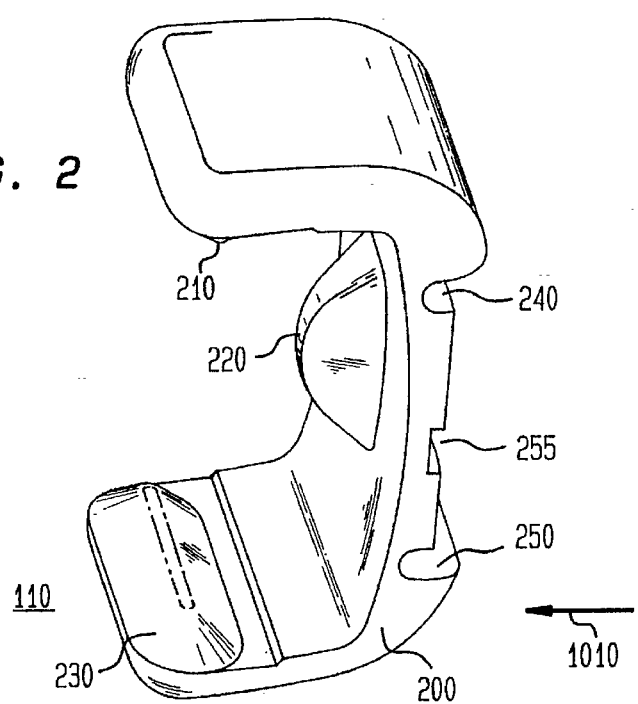
FIG. 2 shows, in pictorial form, a perspective view of a probe clip which is fabricated in accordance with the present invention.

FIG. 2 shows, in pictorial form, a perspective view of probe clip 110 which is fabricated in accordance with the present invention. As shown in FIG. 2, probe clip 110 is comprised of "C" clamp 200. Protuberances 210, 220, and 230 are formed on the inside of "C" clamp 200, which protuberances are fabricated to fit into shallow detents 280, 290, and a detent on the opposite side of ultrasound probe 300 from detent 280 (not shown in FIG. 6). As is shown in FIG. 6, detent 280 is for protuberance 210, a companion detent to detent 280 on the opposite side of ultrasound probe 300 is for protuberance 230, and detent 290 is for protuberance 220. In order to ensure universality of needle guides fabricated in accordance with the present invention, it is required that ultrasound probes be manufactured so that the distance between top detent 280 and its companion detent on the bottom of the probe (for holding protuberances 210 and 230, respectively) and the positioning of side detent 290 (for holding protuberance 220) is manufactured to the same specification for all ultrasound probes. This ensures that one needle guide design will fit all similarly manufactured ultrasound probes. As further shown in FIG. 2, channels 240 and 250 are disposed across the back of "C" clamp 200.

Probe clip 110 is required to flex in order for protuberances 210 and 230 to be able to pushed into the appropriate detents. However, if probe clip 110 is too flexible, it will not hold onto the probe tightly and, if probe clip 110 is too rigid, it may damage the probe when it is pushed onto it or removed from it. As those skilled in the art will readily appreciate, it is possible to fabricate a needle guide without using a probe clip lock. In such an embodiment, the probe clip will be retained on the probe because of the rigidity of the probe clip. However, in the preferred embodiment of the present invention, probe clip 110 is preferably formed of a somewhat rigid material, for example, injection molded plastic, and, as a result, "C" clamp 200 is somewhat rigid. Channels 240 and 250 enable one to flex "C" clamp 200 to a greater extent than would be possible in their absence. This flexing enables probe clip 110 to be more easily detachably affixed to ultrasound probe 300. When probe clip 110 is affixed to ultrasound probe 300, probe clip lock 120 is engaged so that channels 240 and 250 are filled by legs 571 and 572, respectively of probe clip lock 120 (see FIG. 3). When channels 240 and 250 are thusly filled, the flexibility of "C" clamp 200 is greatly reduced and this serves to lock probe clip 110 so it is securely affixed to ultrasound probe 300.

Figure 3:
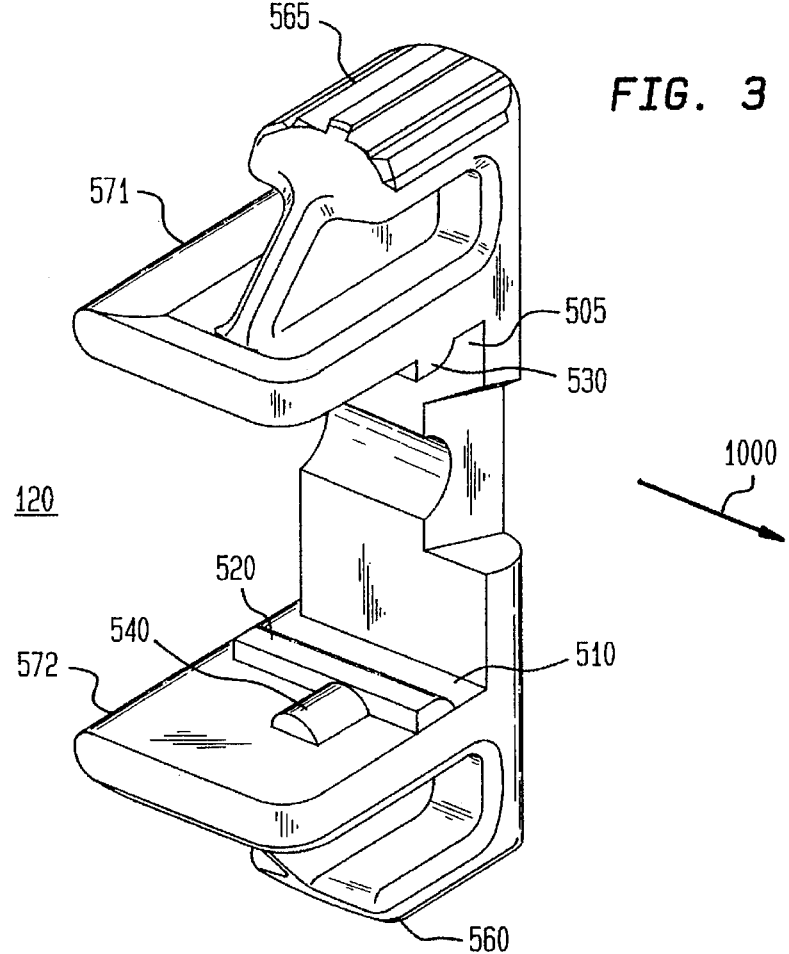
FIG. 3 shows, in pictorial form, a perspective view of a probe clip lock which is fabricated in accordance with the present invention
Figure 4:
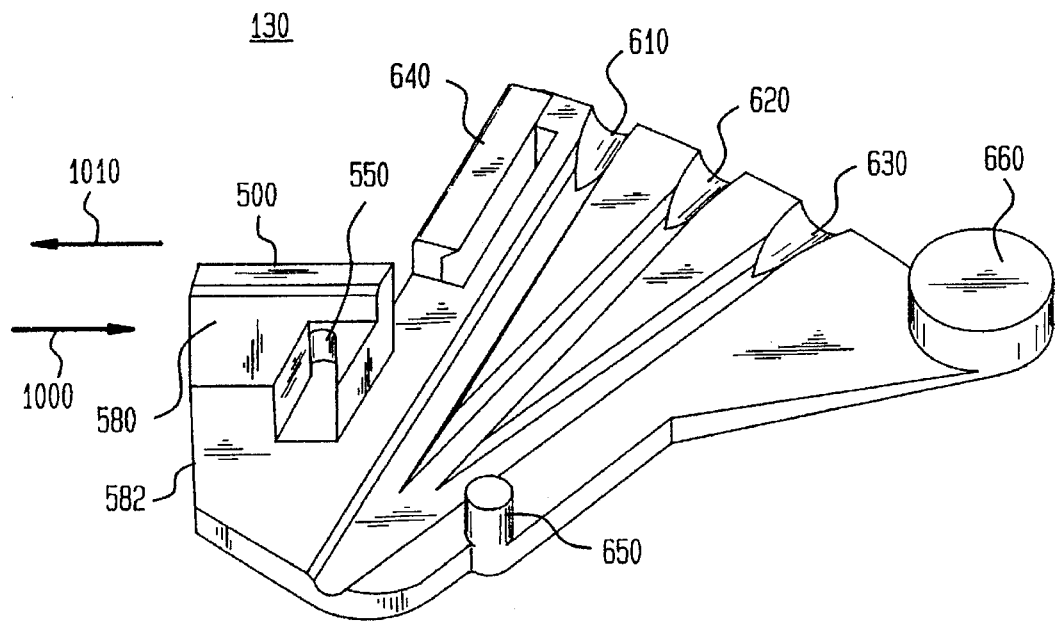
FIG. 4 shows, in pictorial form, a perspective view of a needle support which is fabricated in accordance with the present invention.

FIG. 3 shows, in pictorial form, a perspective view of probe clip lock 120 which is fabricated in accordance with the present invention and FIG. 4 shows, in pictorial form, a perspective view of needle support 130 which is fabricated in accordance with the present invention. Arrow 1000 in FIG. 3 and arrow 1000 in FIG. 4 show the direction that probe clip lock 120 is moved when it is mounted on needle support 130. Platform 500 on needle support 130 (FIG. 4) supports probe clip lock 120 when it is mounted on needle support 130. Platform 500 slides in grooves 505 and 510 on probe clip lock 120 (FIG. 3), which grooves 505 and 510 are formed by protuberances 520 and 530, respectively.

In operation, and when assembled to form needle guide 100, probe clip lock 120 can be located in one of two positions along platform 500 of needle support 130. These two positions are determined by the position of two protuberances on probe clip lock 120—protuberance 540 and a protuberance on leg 571 (not shown in FIG. 3)—with respect to two posts on needle support 130—post 550 and a post on the opposite side of platform 500 (not shown in FIG. 4). Post 550 and its companion post are rigid and they lock probe clip lock 120 in a first position or in a second position, depending on whether the protuberances are disposed on one or the other side of the posts. When urging protuberance 540 on leg 572 and its companion protuberance on leg 571 into the first or second position with respect to post 550 and its companion post, legs 571 and 572 flex to enable the protuberances to be moved past the posts. Extensions 560 and 565 on probe clip lock 120 (shown in FIG. 3) provide support for legs 571 and 572 and they also provide a means for a user to urge probe clip lock 120 into the first position or into the second position.

As further shown in FIG. 4, needle support 130 is further comprised of grooves 610, 620, and 630 for supporting needles. The three grooves are used to support a needle at three different angles for use in performing differing surgical procedures or for providing penetration of a needle to a different depth within a patient's body. Needle support 130 further comprises overhang 640 for holding needle cap 150, post 650 for holding needle cap 150, and protuberance 660 for locking needle cap 150 to needle support 130. Post 650 has an overhang on an inner surface and a flat portion under the overhang for providing a snap fit with needle cap 150. Protuberance 660 also has an overhang on an inner surface and a flat portion under the overhang for providing a snap fit with needle cap 150.

Figure 5:
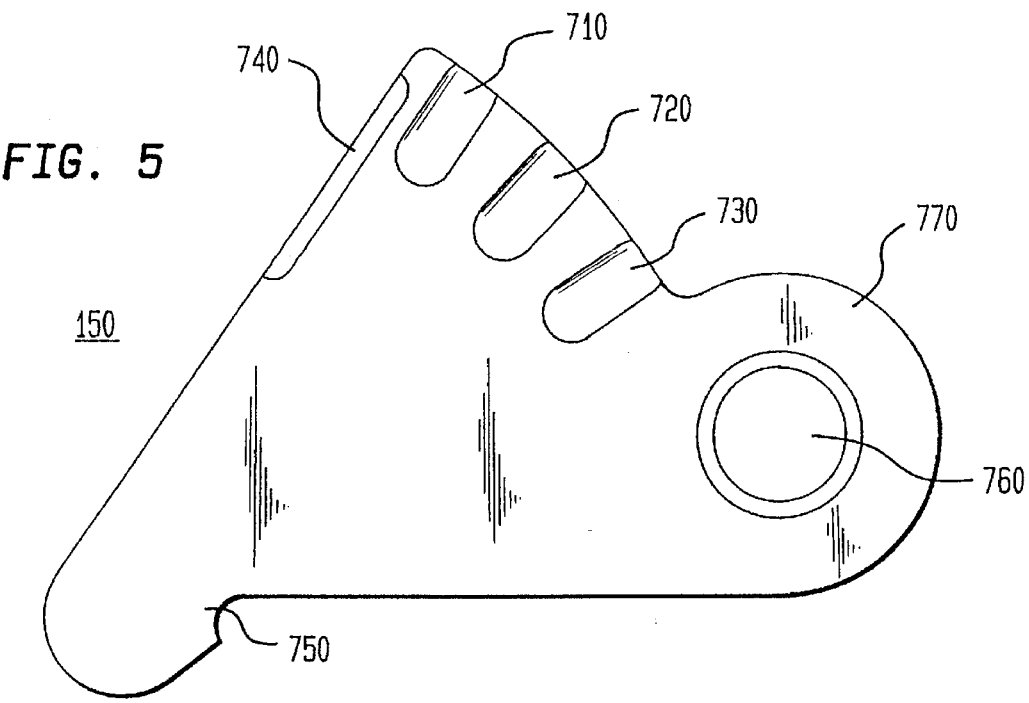
FIG. 5 shows, in pictorial form, a top view of needle cap which is fabricated in accordance with the present invention.

FIG. 5 shows, in pictorial form, a top view of needle cap 150 which is fabricated in accordance with the present invention. As shown in FIG. 5, needle cap 150 is substantially flat. Area 740 along one edge of needle cap 150 is slanted so that the edge along area 740 is thinned with respect to the rest of needle cap 150. When needle cap 150 is mated with needle support 130, area 740 slips under a ledge formed by overhang 640 on needle support 130. As further shown in FIG. 5, indented arc 750 is formed along an edge of needle cap 150. The edge along arc 750 is slanted so that the edge along arc 750 is thinned with respect to the rest of needle cap 150. When needle cap 150 is mated with needle support 130, arc 750 fits about post 650, and under the overhang formed on post 650, to provide stability and a snap fit.

Grooves 710, 720, and 730 are formed on the bottom surface of needle cap 150 and are disposed along the entire length of needle cap 150. To provide needle guides, grooves 710, 720, and 730 on needle cap 150 align with grooves 610, 620, and 630, respectively, on needle support 130 when needle cap 150 is mated with needle support 130. Lastly, needle cap 760 has aperture 760 disposed within its body which aligns with protuberance 660. The inner edge of aperture 760 is slanted so that the edge along aperture 760 is thinned with respect to the rest of needle cap 150. Porch 770 surrounding aperture 760 provides an extension which is advantageously held when needle cap 150 is decoupled from needle support 130 in the manner described below. When needle cap 150 is mated with needle support 130, aperture 760 fits about protuberance 660 and the edge fits under the overhang formed on protuberance 660 to provide stability and a snap fit.

Needle guide 100 is assembled, after the above-described components are fabricated by injection molding, by mounting probe clip lock 120 on needle support 130 as was described above. Then, needle support 130 is abutted to "C" clamp 110 along the direction shown by arrow 1010 in FIG. 2 and arrow 1010 in FIG. 4. Edges 580 and 582 shown in FIG. 4 form a "T" which is abutted to "T" depression 255 in "C" clamp 110. Then, the two pans are ultrasonically welded together. Those skilled in the art understand that embodiments of the present invention are not limited to those which are fabricated in this manner and that embodiments of the present invention may be fabricated utilizing other methods.

In order to insert a needle into needle guide 100, one assembles the needle guide by snapping needle cap 150 into place over needle support 130. Then, a needle is inserted into a desired one of the apertures formed by the combinations of grooves (610,710), (620,720), and (630,730).

A needle may be removed easily and quickly by a user with one hand. To do this, a user presses protuberance 660, for example, with a thumb, and holds needle cap 150, for example, with a forefinger. This causes needle cap 150 and needle support 130 to be decoupled and needle cap 150 to be held about porch 770 between the forefinger and the thumb. Then, the needle may be lifted away from needle support 130 or vice versa.

Although various modifications may be suggested by those versed in the art, it should be understood that we wish to embody within the scope of the patent granted hereon all such modification as reasonably and properly come within the scope of our contribution to the art. For example, other means for locking the probe clip to the ultrasound probe may be used and other means for mating the needle cap to the needle support may be used. In addition, different size needles may be used by providing a new needle cap 150 wherein the size of the grooves 710, 720, and 730 in the new needle cap are changed to accommodate the different size needles. Further, embodiments of the present invention may be fabricated wherein grooves are fabricated in either of, but not both, of needle support 130 and needle cap 150.

Although embodiments of the present invention have been described as pertaining to a needle guide, the present invention is not limited to a needle guide. For example, embodiments of the present invention may be used to guide apparatus such as radio frequency cauterization probes, radio isotope beads, and any number of similar devices.

What is claimed is:

1. A device guide for use with a probe comprises:
   clip means for detachably affixing the device guide to the probe, the clip means comprising a C-clamp, the C-clamp comprising protuberances disposed along an inner arc of the C-clamp, the C-clamp defining one or more channels along an outer arc of the C-clamp;

clip locking means for detachably locking the clip means to secure the device guide to the probe, wherein the clip lock means comprises one or more legs which are disposed to be moved to fill at least a portion of the channels to lock the clip means and, thereby to secure the device guide to the probe;

device support means, affixed to the clip means, for supporting and positioning a device; and device cap means, detachably affixed to the device support means, for supporting and positioning the device;

wherein the device support means and the device cap means are comprised of snap locking means for detachably affixing the device support means and the device cap means to each other.

2. A device guide for use with a probe comprising:

clip means for detachably affixing the device guide to the probe;

clip lock means for detachably locking the clip means to secure the device guide to the probe;

device support means, affixed to the clip means, for supporting and positioning a device; and device cap means, detachably affixed to the device support means, for supporting and positioning the device; wherein the device support means and the device cap means are comprised of snap locking means for detachably affixing the device support means and the device cap mean to each other; and the device support means and the device cap means each comprise a plurality of grooves, which grooves are disposed over one another to form a plurality of channels when the device support means and device cap means are affixed to each other, each one of the channels orienting the device in a different position, the plurality of channels defining a common exit for the device.

3. A needle guide apparatus for use with an ultrasound probe, the guide comprising:

a clamp for releasably attaching to an ultrasound probe;

a needle guide body for receiving and supporting a needle; and a clamp locking mechanism for locking the clamp to the ultrasound probe and for coupling to the needle guide body; and wherein the clamp defines a C-shaped opening for receiving the ultrasound probe and defines a channel for decreasing clamp rigidity; and wherein the clamp locking mechanism comprises a protrusion mating with at least a portion of the clamp channel to lock the clamp to the ultrasound probe.

4. The needle guide apparatus of claim 3, wherein the clamp locking mechanism defines two positions among which the needle guide body is locked to the clamp locking mechanism.

5. The needle guide apparatus of claim 4 in which the clamping locking mechanism comprises two protuberances and in which the needle guide body comprises two posts, and in which a first of the two positions is defined by relatively positioning the two protuberances on one side of the two posts, and in which a second of the two positions is defined by relatively positioning the two protuberances on another side of the two posts.

6. The needle guide of claim 3 in which the needle guide body defines a plurality of non-parallel grooves, each one of the plurality of non-parallel grooves having a unique opening for receiving a needle, each one of the grooves extending to a common opening at which the needle exits once received.

7. The needle guide of claim 3 in which the needle guide body comprises two pieces which snap together.

8. A needle guide apparatus for use with an ultrasound probe, the guide comprising:

a clamp for releasably attaching to an ultrasound probe;

a needle guide body for receiving and supporting a needle; and a clamp locking mechanism for locking the clamp to the ultrasound probe and for coupling to the needle guide body; and wherein the needle guide body defines a plurality of non-parallel grooves, each one of the plurality of non-parallel grooves having a unique opening for receiving a needle, each one of the grooves extending to a common opening at which the needle exits once received.

9. The needle guide apparatus of claim 8, wherein the clamp locking mechanism defines two positions among which the needle guide body is locked to the clamp locking mechanism.

10. The needle guide apparatus of claim 9 in which the clamping locking mechanism comprises two protuberances and in which the needle guide body comprises two posts, and in which a first of the two positions is defined by relatively positioning the two protuberances on one side of the two posts, and in which a second of the two positions is defined by relatively positioning the two protuberances on another side of the two posts.

11. The needle guide apparatus of claim 9 wherein the clamp defines a C-shaped opening for receiving the ultrasound probe and defines a channel for decreasing clamp rigidity; and wherein the clamp locking mechanism comprises a protrusion mating with at least a portion of the clamp channel to lock the clamp to the ultrasound probe.

* * * * *